US012558111B2

(12) United States Patent
Hales et al.

(10) Patent No.: US 12,558,111 B2
(45) Date of Patent: Feb. 24, 2026

(54) POLYAXIAL DRILL GUIDE

(71) Applicant: CARTIVA, INC., Alpharetta, GA (US)

(72) Inventors: Richard Clay Hales, Alpharetta, GA (US); Guixin Zhang, Atlanta, GA (US); Moriah Ellen Mattson, Marietta, GA (US)

(73) Assignee: STRYKER CORPORATION, Portage, MI (US)

( * ) Notice: Subject to any disclaimer, the term of this patent is extended or adjusted under 35 U.S.C. 154(b) by 669 days.

(21) Appl. No.: 17/758,604

(22) PCT Filed: Jan. 12, 2021

(86) PCT No.: PCT/US2021/013019
§ 371 (c)(1),
(2) Date: Jul. 11, 2022

(87) PCT Pub. No.: WO2021/183210
PCT Pub. Date: Sep. 16, 2021

(65) Prior Publication Data
US 2023/0035385 A1 Feb. 2, 2023

Related U.S. Application Data

(60) Provisional application No. 62/987,502, filed on Mar. 10, 2020.

(51) Int. Cl.
*A61B 17/17* (2006.01)
(52) U.S. Cl.
CPC .............................. *A61B 17/1775* (2016.11)

(58) Field of Classification Search
CPC ............ A61B 17/1775; A61B 17/1728; A61B 17/1739; A61B 17/1757; A61B 17/1764; A61B 17/1782; A61B 17/17; A61B 17/15
See application file for complete search history.

(56) References Cited

U.S. PATENT DOCUMENTS

| | | | |
|---|---|---|---|
| 6,066,142 A | 5/2000 | Serbousek et al. | |
| 7,731,721 B2 | 6/2010 | Rathbun et al. | |

(Continued)

FOREIGN PATENT DOCUMENTS

| | | |
|---|---|---|
| CA | 3101460 A1 | 1/2020 |
| CN | 104905846 B | 6/2017 |
| CN | 110868963 A | 3/2020 |

OTHER PUBLICATIONS

Partial European Search Report issued in connection with corresponding European Patent Application No. 21768386.1, Nov. 23, 2023, 13 pages.

(Continued)

*Primary Examiner* — Amy R Sipp
(74) *Attorney, Agent, or Firm* — DUANE MORRIS LLP

(57) ABSTRACT

An orthopedic drill guide assembly is disclosed. The assembly can include an elongated shaft having a proximal end and a distal end, and a first guide member that includes a bone-contacting surface and a second surface opposite the bone-contacting surface. The first guide member is provided at the distal end of the elongated shaft. The first guide member includes one or more guide holes that are configured for receiving a drill bit at an angle that can vary from 0 to 30 degrees from orthogonal of the bone-contacting surface.

13 Claims, 11 Drawing Sheets

(56)                    References Cited

U.S. PATENT DOCUMENTS

| | | | |
|---|---|---|---|
| 7,763,029 | B2 | 7/2010 | Rathbun et al. |
| 2001/0047172 | A1 | 11/2001 | Foley et al. |
| 2003/0083667 | A1 | 5/2003 | Ralph et al. |
| 2004/0186482 | A1 | 9/2004 | Kolb et al. |
| 2004/0267274 | A1 | 12/2004 | Patel et al. |
| 2005/0085818 | A1* | 4/2005 | Huebner ............ A61B 17/1728 |
| | | | 606/291 |
| 2007/0055286 | A1 | 3/2007 | Ralph et al. |
| 2008/0077152 | A1 | 3/2008 | McClintock et al. |
| 2008/0154274 | A1* | 6/2008 | Claypool ............... A61B 17/17 |
| | | | 606/96 |
| 2009/0024132 | A1 | 1/2009 | Blain et al. |
| 2010/0130983 | A1 | 5/2010 | Thornhill et al. |
| 2011/0224737 | A1 | 9/2011 | Lewis et al. |
| 2013/0012952 | A1 | 1/2013 | Fallin et al. |
| 2013/0211462 | A1 | 8/2013 | Walker |
| 2013/0289626 | A1* | 10/2013 | Murashko, Jr. ........ A61B 17/88 |
| | | | 606/280 |
| 2014/0074174 | A1* | 3/2014 | Schacherer ........ A61B 17/8061 |
| | | | 606/86 R |
| 2014/0343403 | A1* | 11/2014 | Kunz ................. A61B 17/1703 |
| | | | 600/424 |
| 2015/0282819 | A1* | 10/2015 | Austin ................... A61B 17/17 |
| | | | 606/96 |
| 2019/0125367 | A1* | 5/2019 | Acevedo ........... A61B 17/1796 |
| 2019/0380783 | A1 | 12/2019 | Gemon et al. |

OTHER PUBLICATIONS

International Search Report and Written Opinion for PCT International Application No. PCT/US2021/013019 dated Mar. 25, 2021.
Extended European Search Report issued in connection with corresponding European Patent Application No. 21768386.1, Jan. 25, 2024, 14 pages.

* cited by examiner

C

142

147

143a

149

143b

C

120

121

140b

142

D

147

143a

140

143b

140a

SECTION C-C

157

159

152

150

150

157

SECTION A-A

SECTION B-B

POLYAXIAL DRILL GUIDE

This application is a National Stage Application, filed under 35 U.S.C. 371, of International Patent Application No. PCT/US2021/013019, filed on Jan. 12, 2021, which claims the benefit of U.S. Provisional Application Ser. No. 62/987, 502, filed on Mar. 10, 2020, the entireties of which are incorporated herein by reference.

FIELD OF DISCLOSURE

The present disclosure relates generally to bone screw drill targeting guides that can be used in surgical procedures for joint cartilage repair.

BACKGROUND

In order to install a cartilage surface repairing implant for an articulating surface of a bone in a joint, holes for one or more bone screws for securing the implant need to be pre-drilled into a bone surface. In many types of such implants, specialized drill targeting guides may be required to locate and drill the holes for bone screws.

SUMMARY

An orthopedic drill guide assembly is disclosed. The assembly comprises an elongated shaft having a proximal end and a distal end, and a first guide member comprising a bone-contacting surface and a second surface opposite the bone-contacting surface. The first guide member is provided at the distal end of the elongated shaft, where the first guide member comprises one or more guide holes that are configured for receiving a drill bit at an angle that can vary from 0 to 30 degrees from orthogonal to the bone-contacting surface.

The orthopedic drill guide assembly can further comprise a second guide member comprising one or more guide lumens. The number of guide lumens provided are the same as the number of guide holes in the first guide member. The guide lumens are configured for guiding drill bits at one fixed angle, and the second guide member is configured to fit over the first guide member, whereby the guide lumens are aligned with their respective guide holes.

BRIEF DESCRIPTION OF THE DRAWINGS

The various embodiments of the inventive subject matter of the present disclosure will be described in more detail in conjunction with the following drawing figures. The structures in the drawing figures are illustrated schematically, and they are not necessarily drawn to scale. The drawings figures are not intended to show actual dimensions.

DETAILED DESCRIPTION

Figure 1:
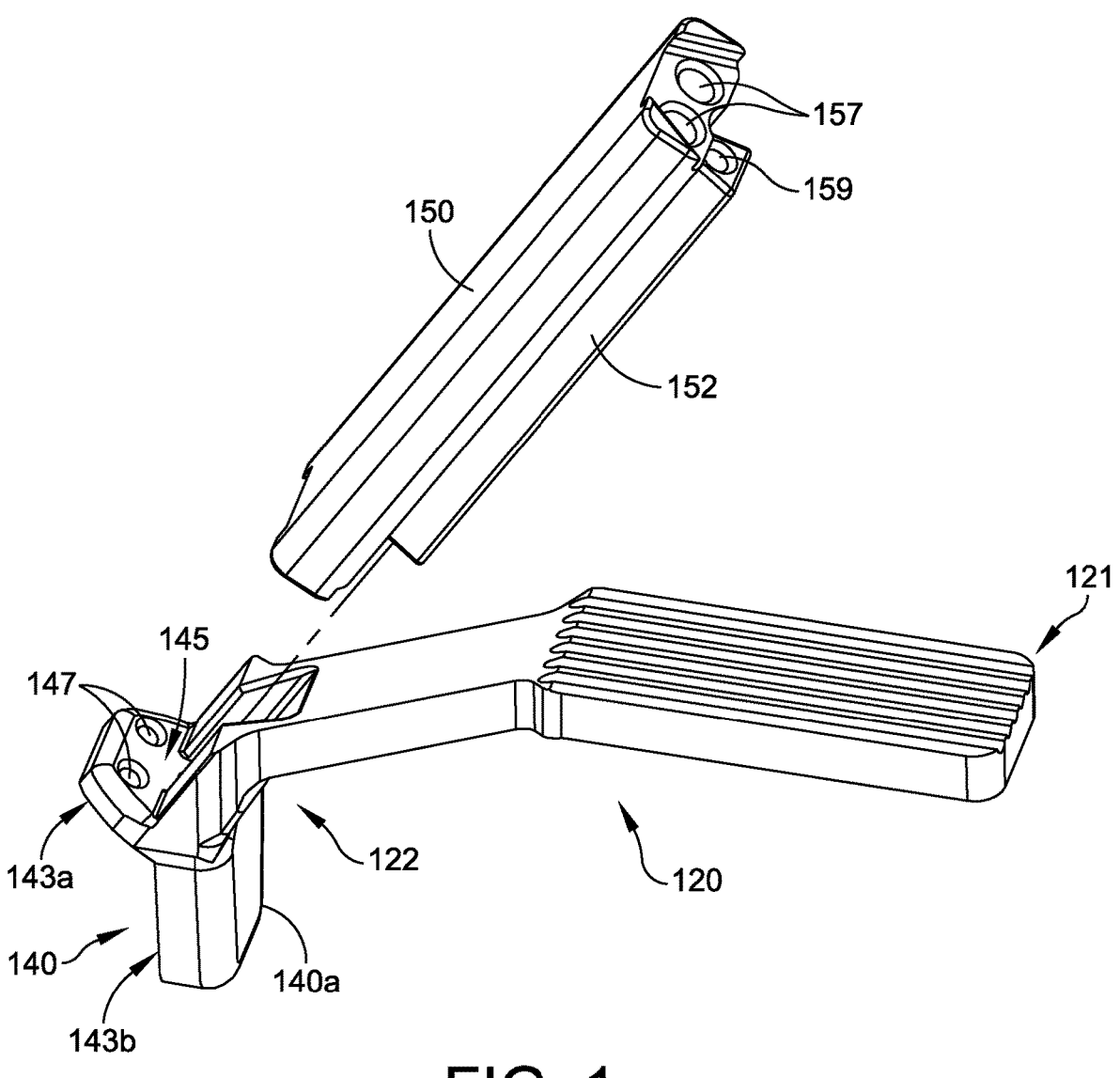
FIG. 1 is a perspective view of the drill guide assembly of the present disclosure.

This description of the exemplary embodiments is intended to be read in connection with the accompanying drawings, which are to be considered part of the entire written description. The drawing figures are not necessarily to scale, and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Referring to FIG. 1, an orthopedic drill guide assembly 100 that is configured for guiding pre-drilling of bone screw holes into a cuneiform that has been prepared with a combination of an angled cut and a vertical cut for receiving a joint repair implant is disclosed. The drill guide assembly 100 comprises an elongated shaft 120. The elongated shaft 120 has a proximal (proximal to the person holding the elongated shaft 120) end 121 and a distal end 122. A first guide member 140 is provided at the distal end 122 of the elongated shaft. The first guide member 140 comprises a first bone-contacting surface 143a and a second surface 145 opposite the first bone-contacting surface 143a. The first guide member 140 also comprises one or more guide holes 147 that extend from the second surface 145 to the first bone-contacting surface 143a. The guide holes 147 are configured for receiving a drill bit at an angle that can vary from 0 to 30 degrees from orthogonal to the bone-contacting surface 143a.

In addition to the guide holes 147, the first guide member 140 can also comprise a hole 149 for receiving a fixation pin 400 for securing the first guide member 140 to a bone surface that has been prepared for receiving a joint repair implant. The hole 149 can be seen in FIGS. 2A and 4A. After the first guide member 140 is placed onto a prepared bone surface so that the bone-contacting surface 143a is in flush contact with the prepared bone surface, the first guide member 140 can be anchored to the bone using a fixation pin 400 driven through the hole 149 and into the underlying bone. FIGS. 3A and 3C show this arrangement. In FIGS. 3A and 3C a bone B1 can be seen having a prepared surface B1' for receiving a joint repair implant. The drill guide assembly 100 is applied to the prepared surface B1' of the bone B1. The first bone-contacting surface 143a of the guide member 140 is contacting the prepared surface B1' and a fixation pin 400 driven through the hole 149 and into the bone B1 secures the first guide member 140 in position.

Figure 2A:
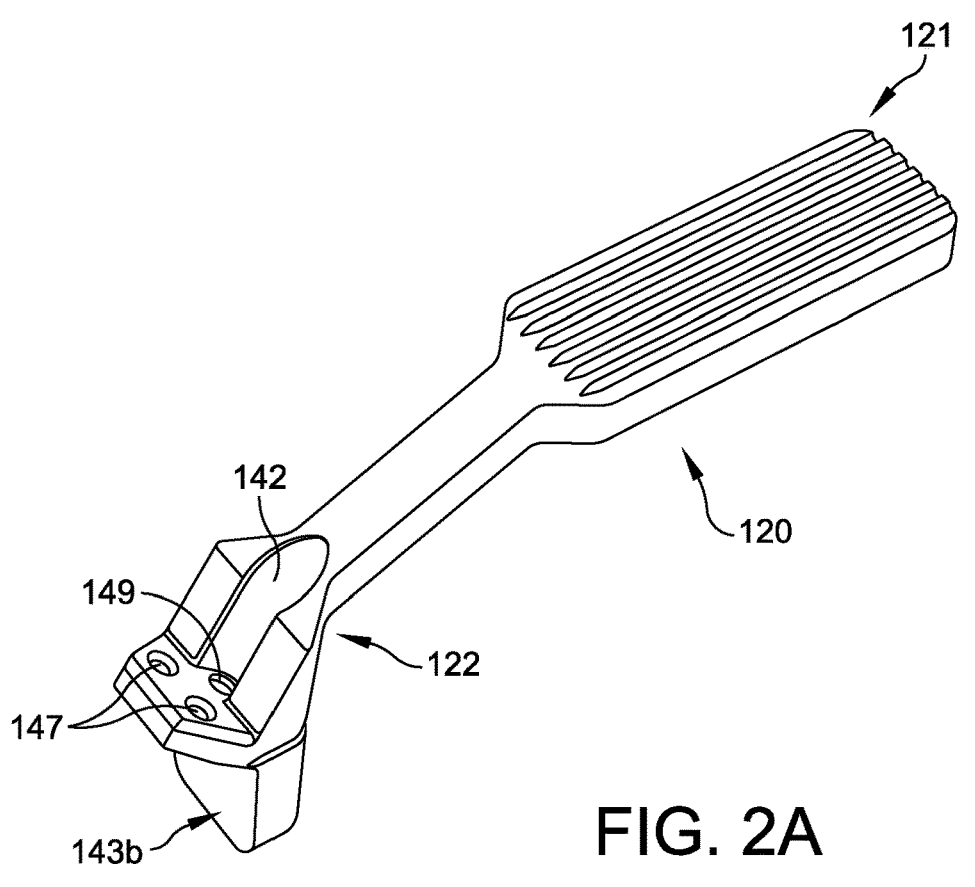
FIGS. 2A and 2B are two perspective views of the first guide portion of the drill guide assembly of the present disclosure.
Figure 2B:
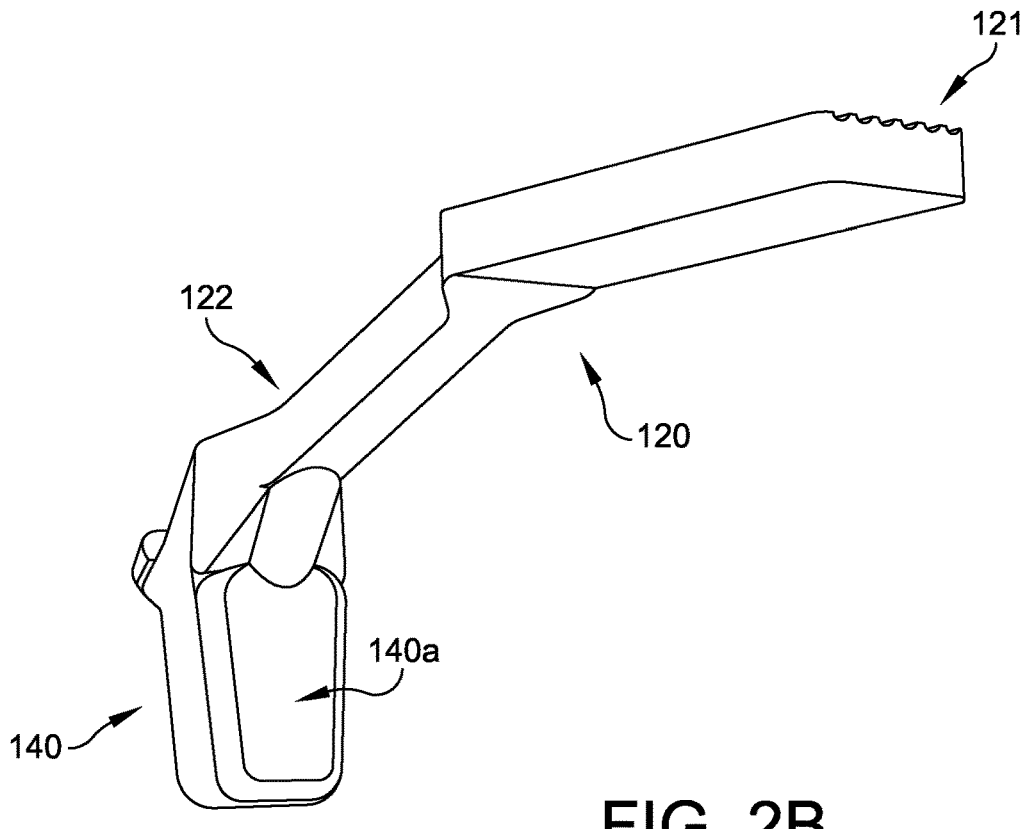
Figure 3A:
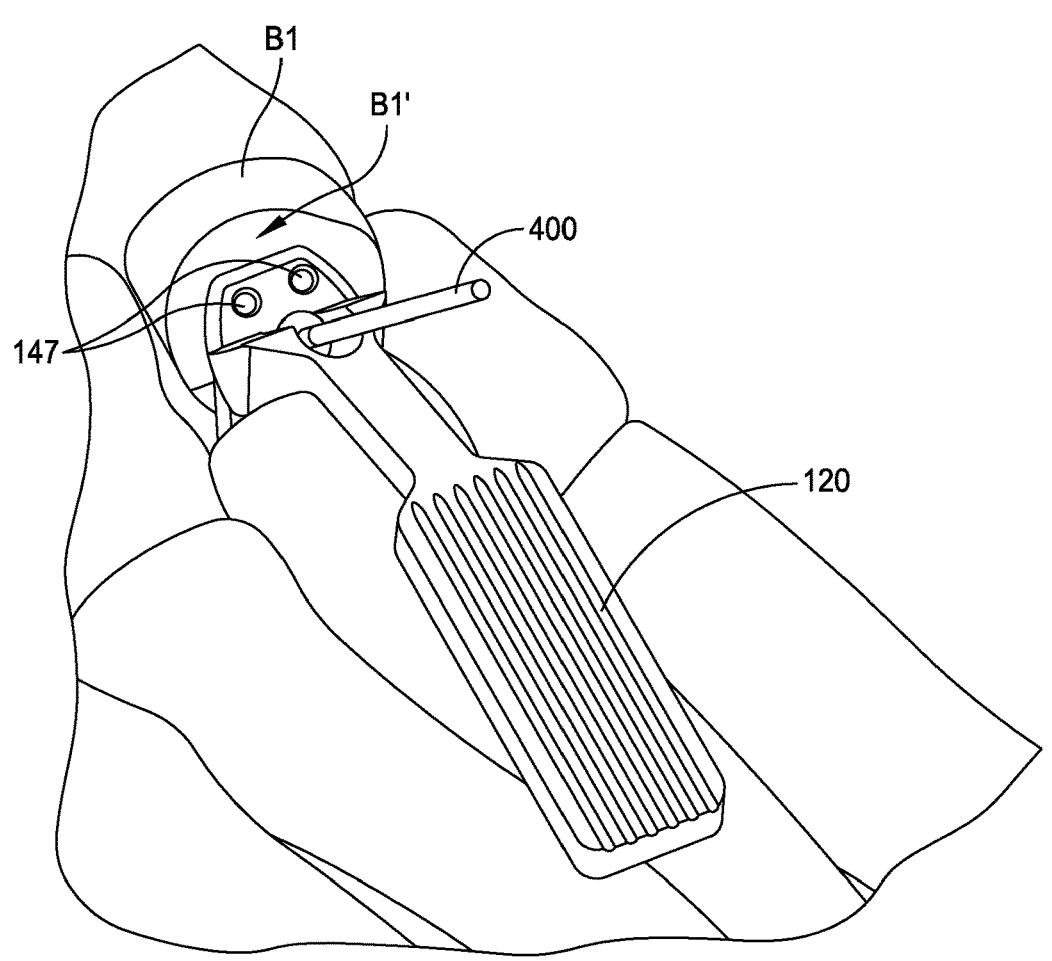
FIG. 3A is an illustration showing the first guide portion in an exemplary application for a cuneiform bone in a TMT joint.
Figure 3B:
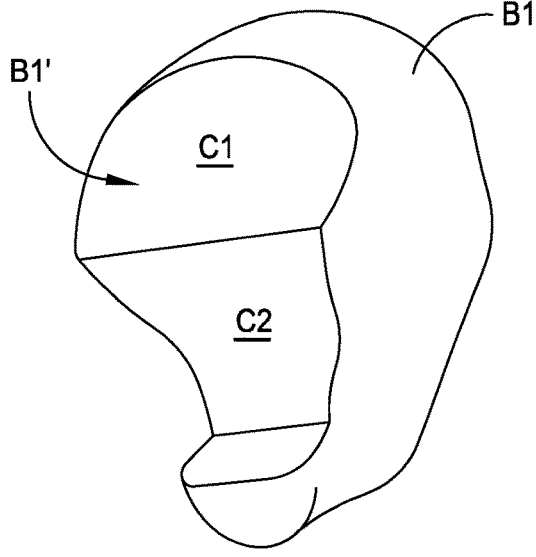
FIG. 3B shows an example of a cuneiform bone that has been prepared to receive a joint repairing implant on which the drill guide of the present disclosure is intended to be used.
Figure 3C:
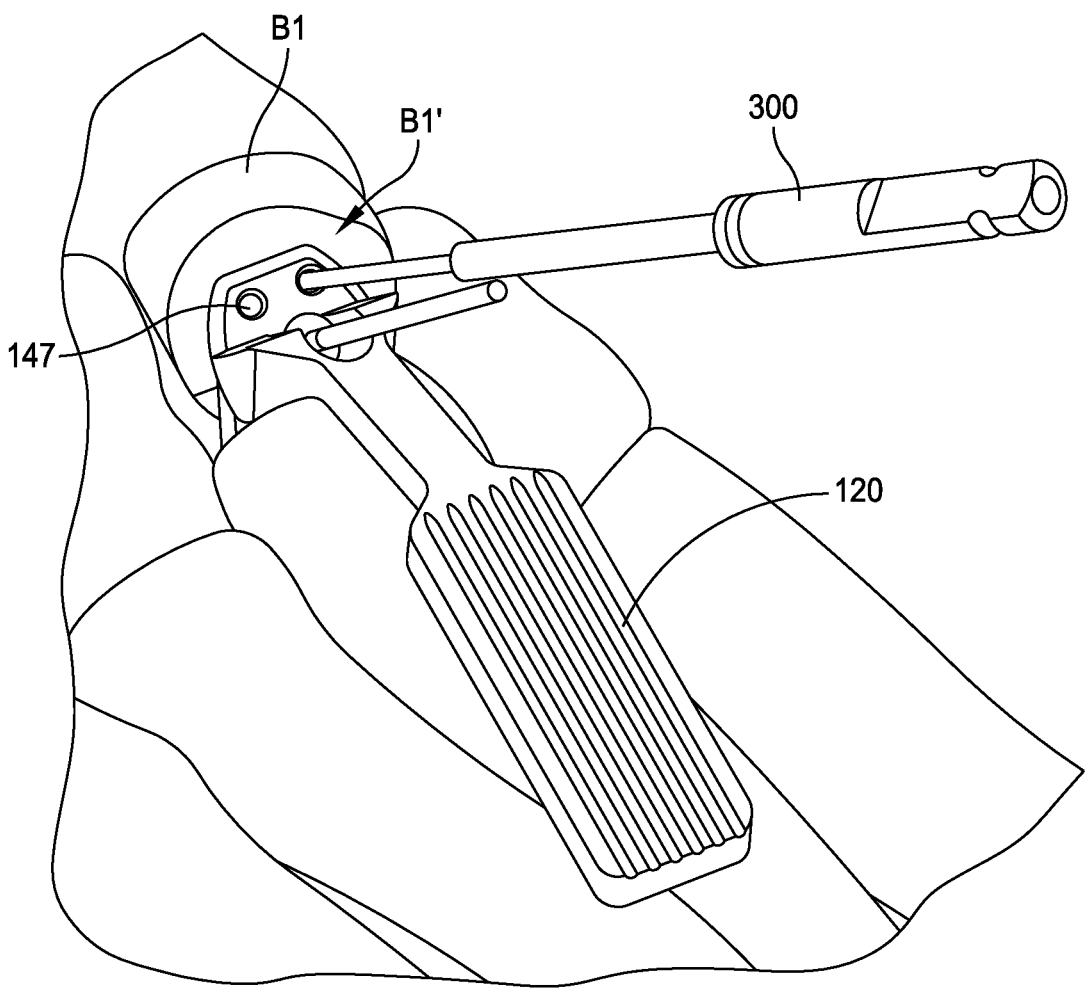
FIG. 3C is another illustration of the arrangement shown in FIG. 3A in which a drill bit is placed through one of the guide holes in the first guide member for pre-drilling a bone screw hole into the cuneiform.
Figure 4A:
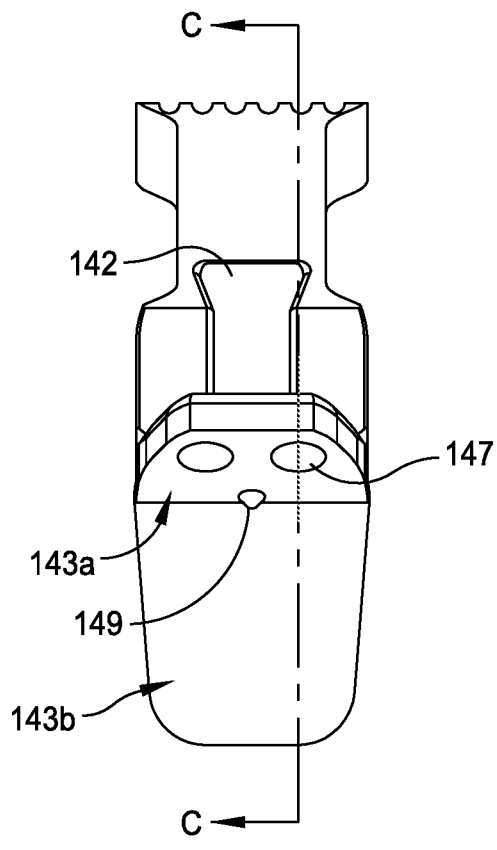
FIG. 4A is a head-on view of the first guide member of the present disclosure.
Figure 4B:
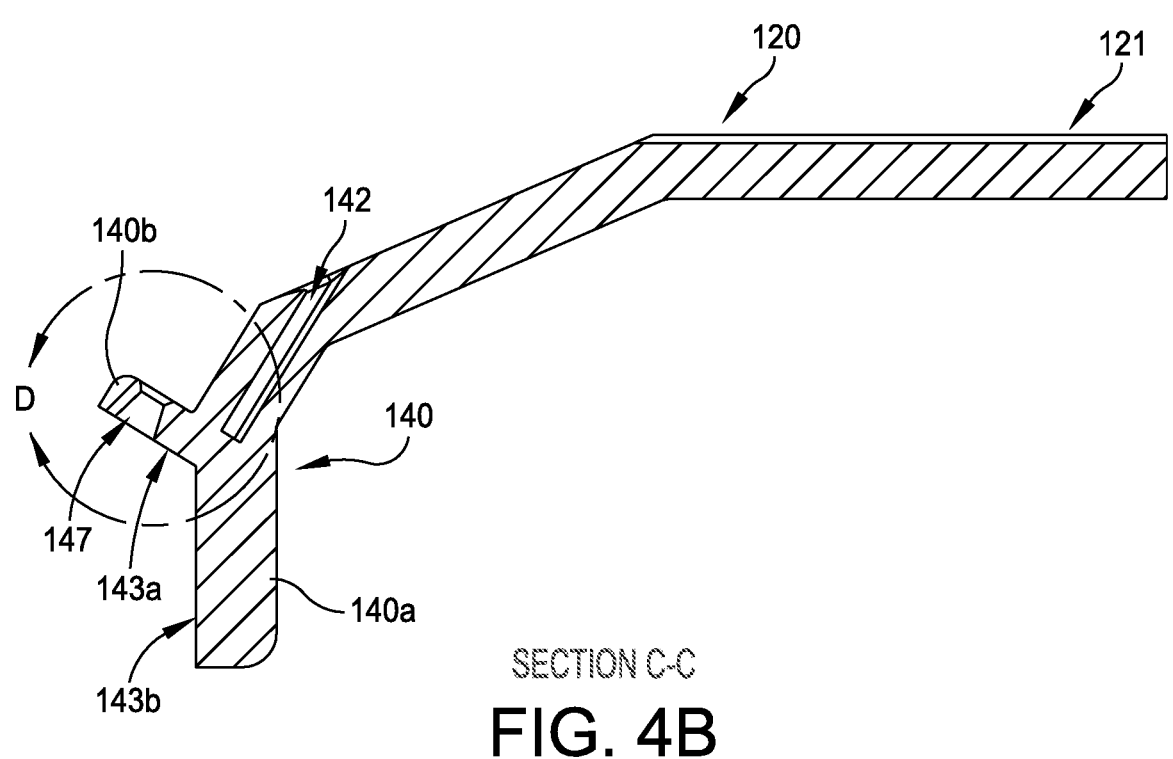
FIG. 4B is a cross-sectional view of the first guide member taken through the section line C-C shown in FIG. 4A.

The first guide member 140 also comprises an extension portion 140a that forms a second bone-contacting surface 143b (see FIGS. 2A and 4B, for example). The second bone-contacting surface 143b intersects the first bone-contacting surface 143a at an angle so that the first bone-contacting surface 143a and the second bone-contacting surface 143b together form a contour that matches the contour of the prepared bone surface B1' that comprises two cut surfaces. In preferred embodiments, the angle formed by the first bone-contacting surface 143a and the second bone-contacting surface 143b is an obtuse angle. FIG. 3B shows an example of such prepared bone surface B1'. The bone B1 exemplified here is a cuneiform bone with its TMT joint surface prepared with two cut surfaces c1 and c2 that form the prepared bone surface B1'.

FIGS. 3A and 3C are illustrations showing the first guide member 140 being used to pre-drill holes for bone screws into a bone B1 to repair the bone's joint surface (i.e. the articulating surface). The bone B1 in this example is a cuneiform at a TMT joint. FIG. 3A shows the first guide member 140 positioned on the prepared bone surface B1' of the bone B1. The first guide member 140 is secured to the bone B1 by a fixation pin 400 that has been placed through the hole 149 in the first guide member 140.

Figure 8:
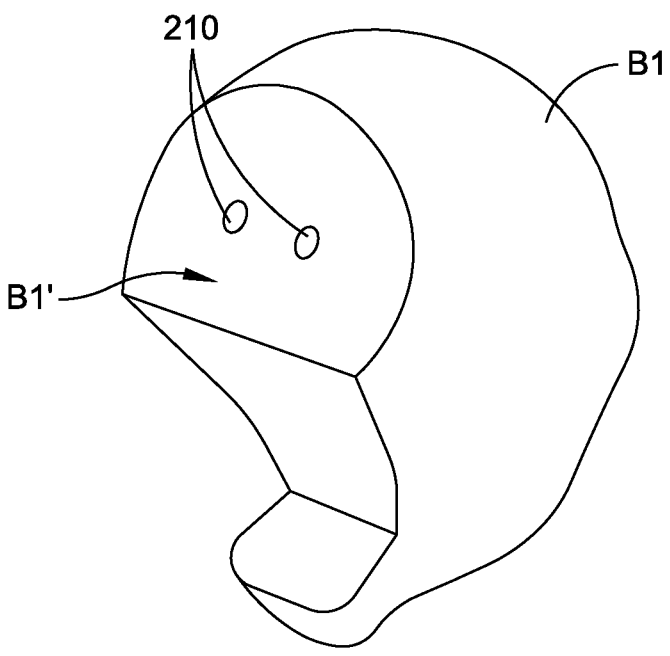
FIG. 8 shows the cuneiform bone of FIG. 3B after two bone screw holes have been pre-drilled using the drill guide assembly of the present disclosure.

FIG. 3C shows a bone screw hole being drilled using a drill bit 300. FIG. 8 shows the cuneiform B1 of FIG. 3B after two bone screw holes 210 have been pre-drilled.

FIGS. 4A-4D are illustrations more detailed views of the structures of the first guide member 140 of the drill guide assembly 100. FIG. 4A shows a head-on view of the first guide member 140 showing the first and second bone-contacting surfaces 143a, 143b, and the guide holes 147 for guiding the drill bit 300 and the hole 149 for the fixation pin 400.

Figure 4C:
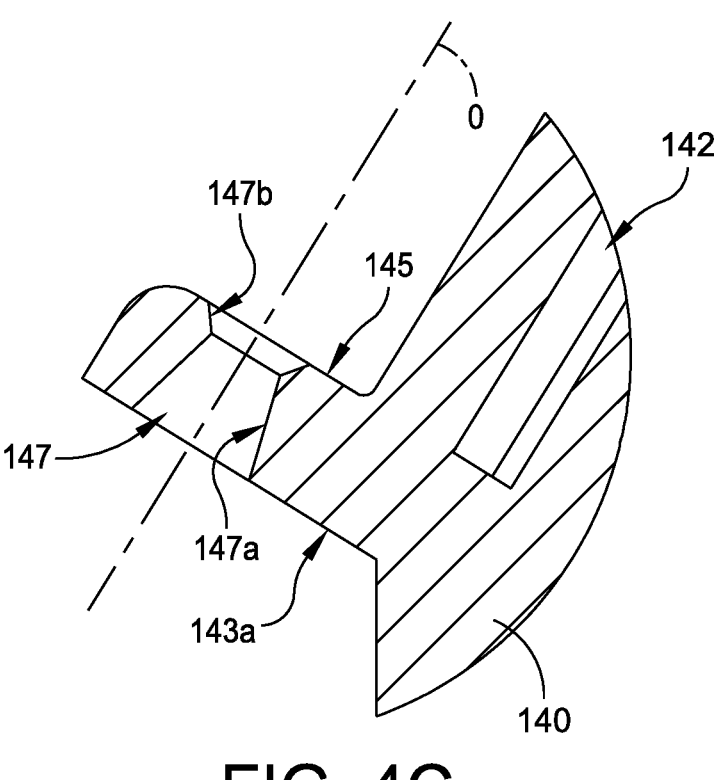
FIGS. 4C and 4D are more detailed views of the area marked as D in FIG. 4B.
Figure 4D:
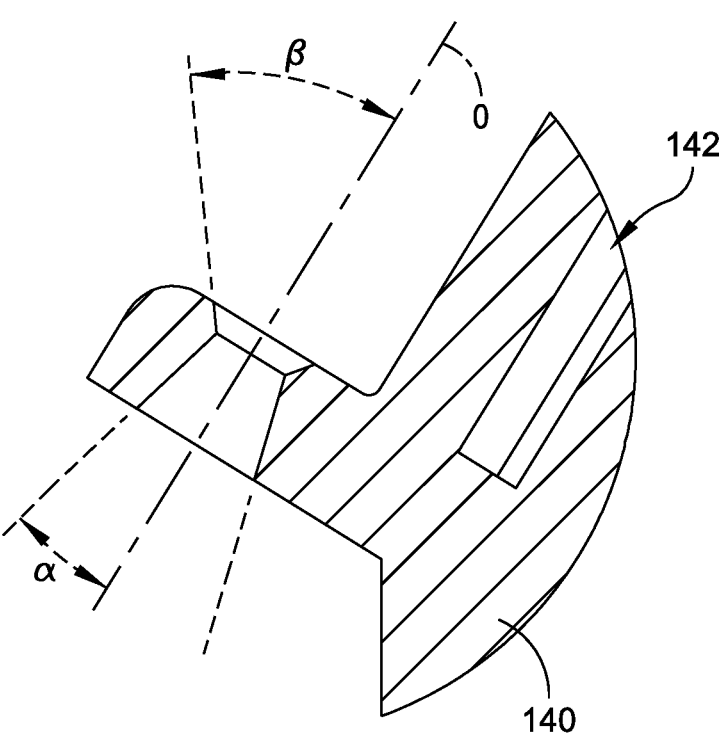

FIG. 4B is a cross-sectional view of the first guide member 140 taken through the section line C-C identified in FIG. 4A. The configuration of one of the guide holes 147 can be seen that allows the angle for the drill bit 300 to vary from 0 to 30 degrees from orthogonal. Orthogonal in this context is with respect to the first bone-contacting surface 143 a. FIG. 4C is a close-up view of the region D identified in FIG. 4B. The interior wall of the guide hole 147 comprises two frustoconical sections 147 a and 147 b. The first frustoconical section 147 a and the second frustoconical section 147 b meet within the thickness of the first guide member 140 between the first bone-contacting surface 143 a and the second surface 145. Both frustoconical sections 147 a and 147 b are configured so that their sidewalls flare out toward the surfaces, the first bone-contacting surface 143 a and the second surface 145. FIG. 4D is another close-up view of the region D identified in FIG. 4B. In FIG. 4D, the angles formed by the sidewalls of the two frustoconical sections 147 a and 147 b and the orthogonal O of the first bone-contacting surface 143 a are identified as $\alpha$ and $\beta$, respectively. In preferred embodiments, the angle $\beta$>the angle $\alpha$. The angle $\beta$ can be from 0 degrees to 30 degrees. In some embodiments, the angle $\beta$ can be from 0 degrees to 15 degrees.

In some embodiments of the drill guide assembly 100, each of the one or more guide holes 147 in the first guide member 140 can have a frustroconical sidewall whose wider opening terminates at the second surface 145 that allows the angle of the drill bit positioned through a guide hole 147 to vary from 0 to 30 degrees from orthogonal to the bone-contacting surface 143 a. The one or more guide holes 147 can also be configured to allow angle of the drill bit to vary from 0 to 15 degrees from orthogonal to the bone-contacting surface.

Figure 5:
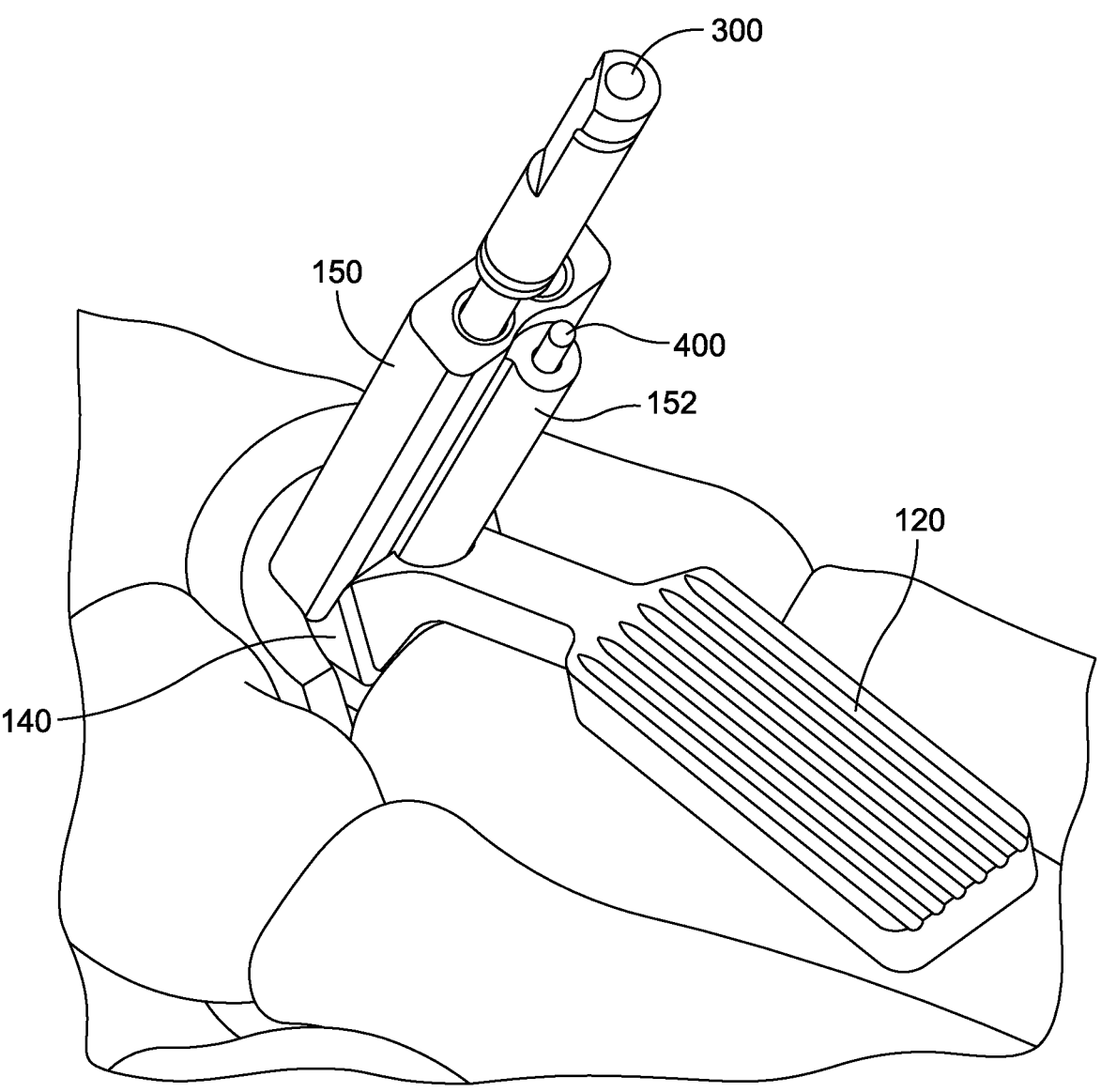
FIG. 5 is an illustration showing the first and second guide portions of the drill guide assembly in a mated configuration according to an embodiment of the present disclosure.

Referring to FIGS. 1, 6A, 6B, and 7A-7D, the drill guide assembly 100 can further comprise a second guide member 150 that is an optional accessory attachment to the first guide member 140. According to some embodiments illustrated in FIGS. 1, 6A, and 6B, the second guide member 150 can comprise an elongated shape and comprises one or more guide lumens 157 extending through its length. The number of guide lumens 157 are the same as the number of guide holes 147 in the first guide member 140. Each of the guide lumens 157 are configured for guiding a drill bit at one fixed angle. The second guide member 150 is configured to fit over the first guide member 140 as shown in FIG. 5. The guide lumens 157 are positioned in the second guide member 150 so that when the second guide member 150 is assembled with the first guide member 140, the guide lumens 157 align with their respective guide holes 147

In some embodiments of the drill guide assembly 100, the one fixed drill bit angle for the guide lumens 157 in the second guide member 150 can be any desired angle. Preferably, the one fixed drill bit angle for the guide lumens 157 is orthogonal to the bone-contacting surface 143a.

Figure 6A:
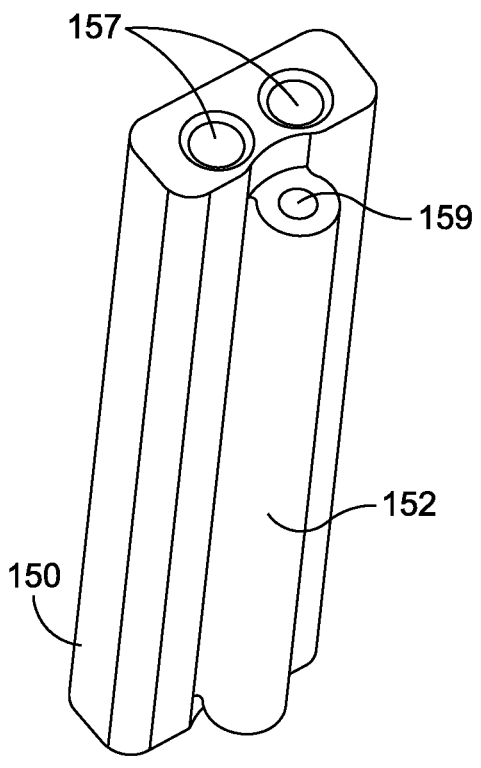
FIGS. 6A-6B are illustrations showing the second guide portion.
Figure 6B:
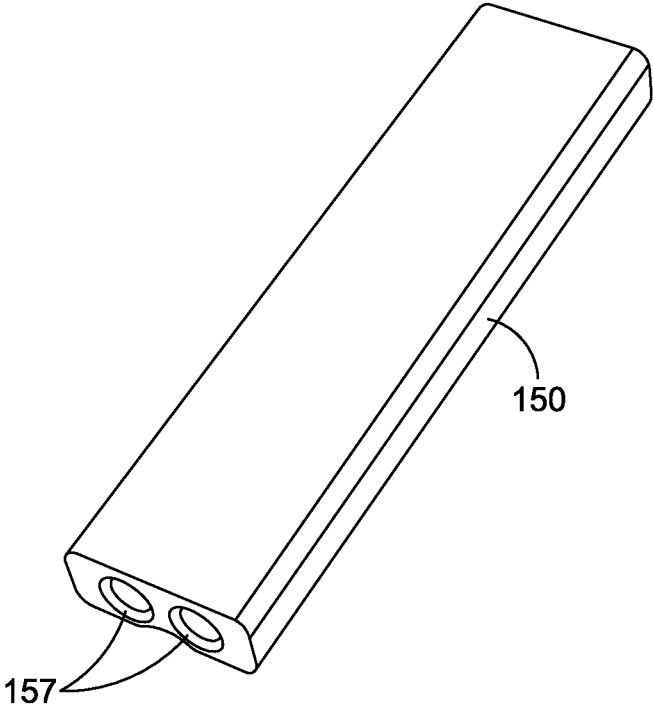
Figure 7A:
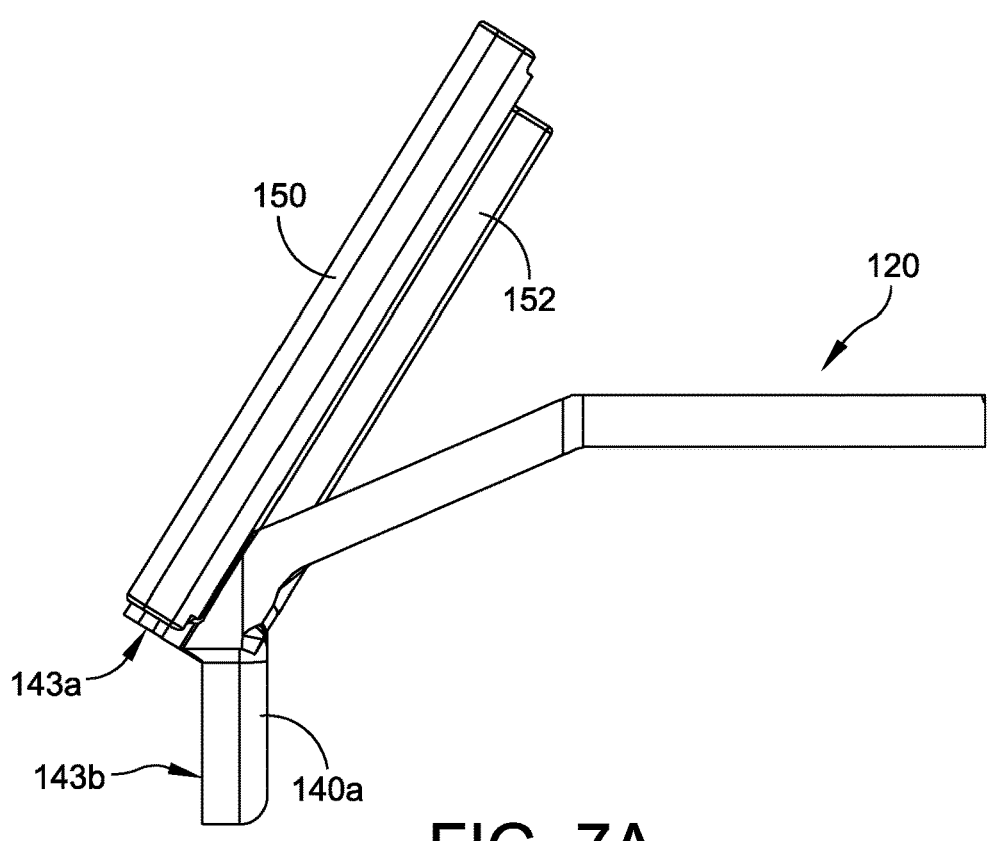
FIG. 7A is a side view of the drill guide assembly in which the first and second guide portions are in the mated configuration.
Figure 7B:
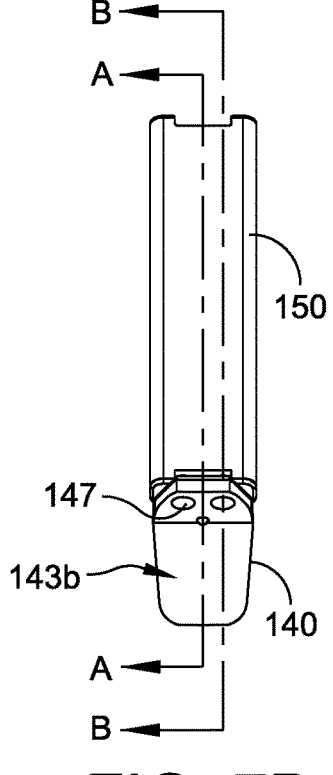
FIG. 7B is a head-on view of the drill guide assembly of FIG. 7A.
Figure 7C:
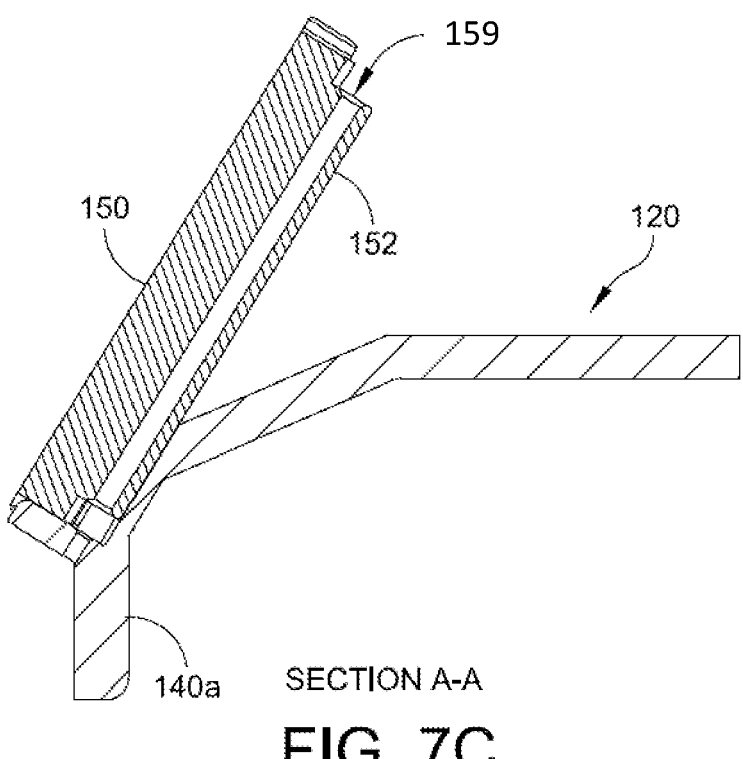
FIG. 7C is a cross-sectional view of the drill guide assembly of FIGS. 7A and 7B taken through the section line A-A shown in FIG. 7B.
Figure 7D:
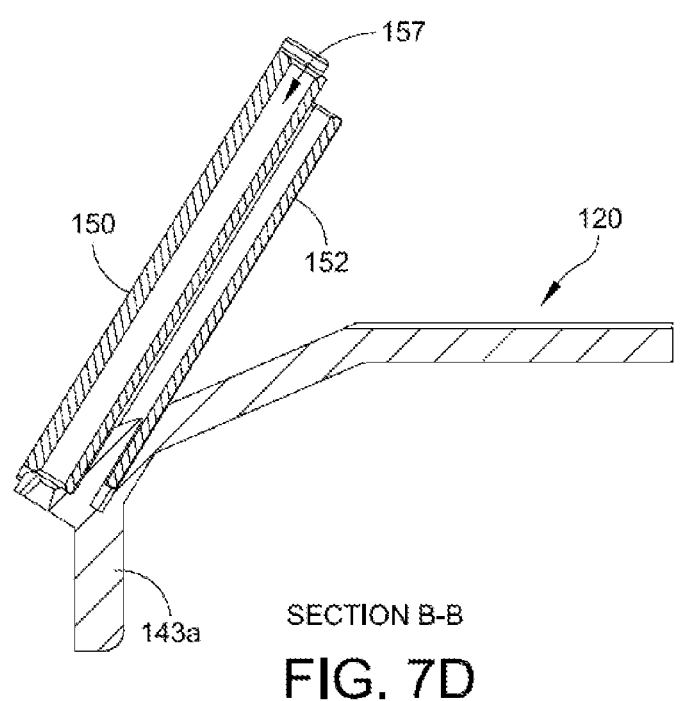
FIG. 7D is a cross-sectional view of the drill guide assembly of FIGS. 7A and 7B taken through the section line B-B shown in FIG. 7B.

Referring to FIGS. 5 and 6A, in some embodiments of the drill guide assembly 100, the second guide member 150 can comprise an alignment key 152 and the first guide member 140 comprises a corresponding alignment key-receiving recess 142. The alignment key 152 and the alignment key receiving recess 142 enable proper fit between the first guide member 140 and the second guide member 150, whereby the guide lumens are aligned with their respective guide holes 147 and also the one fixed drill bit angle for the guide lumens 157 is maintained.

An example of the alignment key 152 and the alignment key-receiving recess 142 configuration is illustrated in FIGS. 1, and 4A-4D. In this embodiment, the alignment key 152 and the alignment key-receiving recess 142 are configured to form a sliding dovetail connection where the alignment key 152 is the tail and the alignment key-receiving recess 142 is the corresponding socket. Another example of the alignment key 152 and the alignment key-receiving recess 142 configuration is illustrated in FIGS. 2A, 3A, 3C, 5, and 6A. In this embodiment, the alignment key 152 forms a protruding cylindrical form and has a rounded contour. The alignment key-receiving recess 142 is a corresponding contour for receiving the alignment key 152. However, these two are merely examples and the alignment key 152 and the alignment key-receiving recess 142 can be configured with other structures that achieve the same function.

FIG. 5 shows the second guide member 150 placed in position over the first guide member 140 by sliding the alignment key 152 into the corresponding alignment key-receiving recess 142. Preferably, the first guide member 140 is first secured to the bone B1 by the fixation pin 400 when the second guide member 150 is slid into place. For such purpose, the alignment key 152 on the second guide member 150 comprises a hole 159 for receiving the fixation pin 400 that is securing the first guide member 140 to the bone B1. In FIG. 5, the fixation pin 400 is visible protruding from the hole 159.

In some embodiments of the drill guide assembly 100, the first guide member 140 and the elongated shaft 120 can be integrally formed. In other embodiments, the first guide member 140 and the elongated shaft 120 can be separate pieced that are configured to be removably coupled to each other.

FIG. 8 shows the cuneiform bone of FIG. 3B after two bone screw holes 210 have been pre-drilled using the drill guide assembly of the present disclosure.

Figure 9:
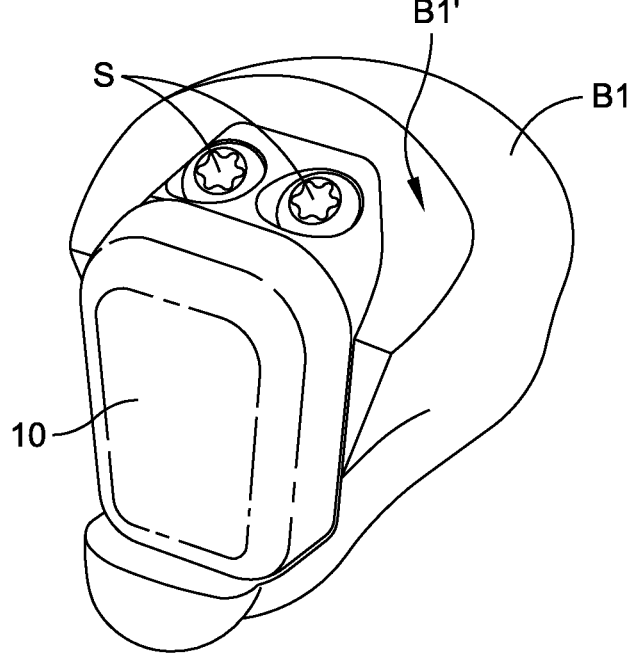
FIG. 9 is an illustration of the cuneiform of FIG. 8, after a joint repair implant has been installed.

FIG. 9 is an illustration of the cuneiform of FIG. 8, after a joint repair implant 10 has been implanted using two bone screws S that are screwed into the two screw holes 210.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

We claim:

1. An orthopedic drill guide assembly comprising:
an elongated shaft having a proximal end and a distal end;
a first guide member provided and integrally formed at the distal end of the elongated shaft, the first guide member comprising:
a first surface configured to contact bone; and
a second surface opposite the first surface, wherein the first guide member comprises one or more guide holes extending from the second surface to the first surface, wherein the one or more guide holes are configured for receiving a drill bit; and
an extension portion comprising:
a third surface, wherein the third surface is substantially planar and configured to contact bone; wherein the third surface intersects the first surface at an angle so that the first surface and the third surface together form a contoured surface configured to match a prepared bone surface that comprises two cut surfaces; and
a second guide member comprising one or more guide lumens,
wherein the number of guide lumens are the same as the number of guide holes in the first guide member,
wherein the one or more guide lumens are configured for guiding drill bits at one fixed angle,
wherein the second guide member is configured to fit over the first guide member, whereby the one or more guide lumens are aligned with their respective guide holes, and
wherein the second guide member comprises an alignment key forming a protruding cylindrical form wherein the alignment key protrudes from a lower surface of the second guide member and the first guide member comprises a corresponding alignment key receiving recess, wherein the alignment key on the second guide member comprises a hole for receiving a guide wire and the first guide member comprises a corresponding hole for the guide wire to pass through so that the alignment key and the alignment key receiving recess enable proper fit between the first guide member and the second guide member, whereby the guide lumens are aligned with their respective guide holes.

2. The drill guide assembly of claim 1, wherein the one or more guide holes are configured for receiving a drill bit at an angle that can be up to 30 degrees from being orthogonal to the first surface.

3. The drill guide assembly of claim 1, wherein each of the one or more guide holes in the first guide member has a frustoconical sidewall whose wider opening terminates at the second surface.

4. The drill guide assembly of claim 1, wherein the one or more guide holes are configured for receiving a drill bit at an angle that is up to 15 degrees from being orthogonal to the first surface.

5. The drill guide assembly of claim 1, wherein the angle formed by the first surface and the third surface is an obtuse angle.

6. An orthopedic drill guide assembly comprising:
an elongated shaft having a proximal end and a distal end;
a first guide member provided at the distal end of the elongated shaft, the first guide member comprising:
a first surface configured to contact bone; and
a second surface opposite the first surface, wherein the first guide member comprises one or more guide holes extending from the second surface to the first surface, wherein the one or more guide holes are configured for receiving a drill bit;
an extension portion comprising:
a third surface, wherein the third surface is substantially planar and configured to contact bone; wherein the third surface intersects the first surface at an angle so that the first surface and the third surface together form a contoured surface configured to match a prepared bone surface that comprises two cut surfaces; and
a second guide member comprising one or more guide lumens,
wherein the number of guide lumens are the same as the number of guide holes in the first guide member,
wherein the one or more guide lumens are configured for guiding drill bits at one fixed angle, wherein the second guide member is configured to fit over the first guide member, whereby the one or more guide lumens are aligned with their respective guide holes, and wherein the second guide member comprises an alignment key forming a protruding cylindrical form wherein the alignment key protrudes from a lower surface of the second guide member and the first guide member comprises a corresponding alignment key receiving recess, wherein the alignment key on the second guide member comprises a hole for receiving a guide wire and the first guide member comprises a corresponding hole for the guide wire to pass through so that the alignment key and the alignment key receiving recess enable proper fit between the first guide member and the second guide member, whereby the guide lumens are aligned with their respective guide holes.

7. The drill guide assembly of claim 6, the one or more guide holes are configured for receiving a drill bit at an angle that can be up to 30 degrees from being orthogonal to the first surface.

8. The drill guide assembly of claim 6, wherein each of the one or more guide holes in the first guide member has a frustoconical sidewall whose wider opening terminates at the second surface.

9. The drill guide assembly of claim 6, wherein the one or more guide holes are configured for receiving a drill bit at an angle that is up to 15 degrees from being orthogonal to the first surface.

10. The drill guide assembly of claim 6, wherein the one fixed angle for the one or more guide lumens is orthogonal to the first surface.

11. The drill guide assembly of claim 6, wherein the first guide member and the elongated shaft are integrally formed.

12. The drill guide assembly of claim 6, wherein the angle formed at the intersection of the first surface and the third surface is an obtuse angle.

13. An orthopedic drill guide assembly comprising:
an elongated shaft having a proximal end and a distal end;
a first guide member provided and integrally formed at the distal end of the elongated shaft, the first guide member comprising:

a first surface configured to contact a first cut surface of a prepared bone surface; and
a second surface opposite the first surface, wherein the first guide member comprises one or more guide holes extending from the second surface to the first surface, wherein the one or more guide holes are configured for receiving a drill bit; and an extension portion comprising:
a third surface, wherein the third surface is configured to contact a second cut surface of the prepared bone surface; wherein:
the first cut surface and the second cut surface are adjacent and form a first angle;
the third surface intersects the first surface at a second angle so that the first surface and the third surface together form a contoured surface, the contoured surface configured to match the first surface to the first cut surface and the second surface to the second cut surface; and a second guide member comprising one or more guide lumens,
wherein the number of guide lumens are the same as the number of guide holes in the first guide member,
wherein the one or more guide lumens are configured for guiding drill bits at one fixed angle,
wherein the second guide member is configured to fit over the first guide member, whereby the one or more guide lumens are aligned with their respective guide holes, and
wherein the second guide member comprises an alignment key forming a protruding cylindrical form wherein the alignment key protrudes from a lower surface of the second guide member and the first guide member comprises a corresponding alignment key receiving recess, wherein the alignment key on the second guide member comprises a hole for receiving a guide wire and the first guide member comprises a corresponding hole for the guide wire to pass through so that the alignment key and the alignment key receiving recess enable proper fit between the first guide member and the second guide member, whereby the guide lumens are aligned with their respective guide holes.

* * * * *